Figure 1:
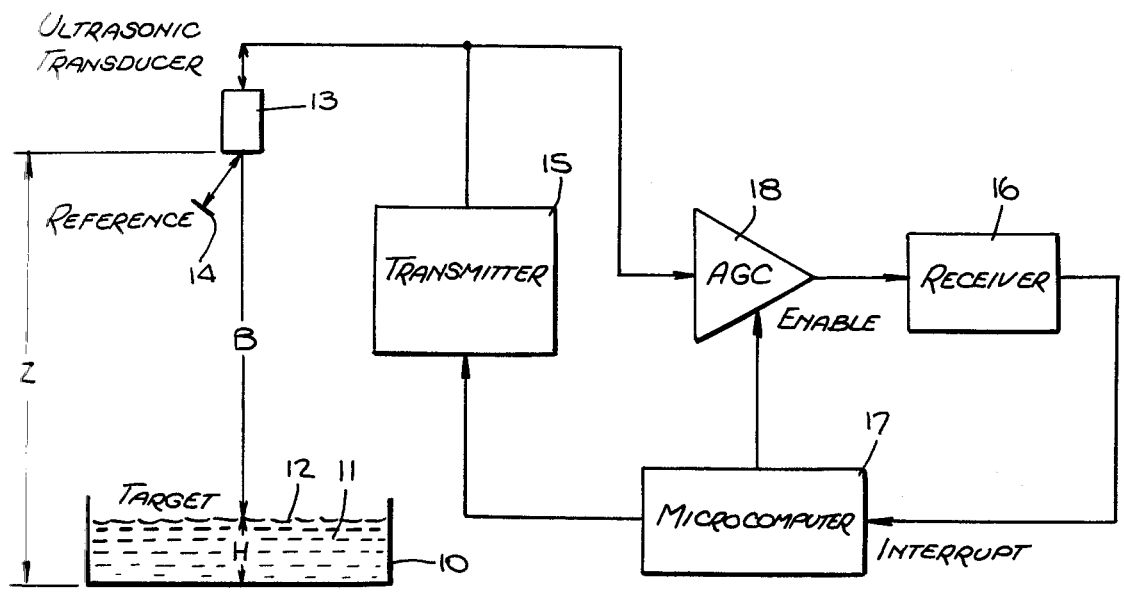

United States Patent [19]

Soltz

[11] Patent Number: 4,578,997
[45] Date of Patent: * Apr. 1, 1986

[54] TIME-SHAPED AGC FOR ULTRASONIC LIQUID LEVEL METER OF THE ECHO-RANGING TYPE

[75] Inventor: Daniel J. Soltz, Norristown, Pa.

[73] Assignee: Fischer & Porter, Warminster, Pa.

[*] Notice: The portion of the term of this patent subsequent to Sep. 11, 2001 has been disclaimed.

[21] Appl. No.: 636,023

[22] Filed: Jul. 30, 1984

Related U.S. Application Data

[63] Continuation-in-part of Ser. No. 337,082, Jan. 4, 1982, Pat. No. 4,470,299.

[51] Int. Cl.[4] .................. G01F 23/28; G01S 15/08
[52] U.S. Cl. .................. 73/290 V; 73/631; 73/900; 367/108; 367/908
[58] Field of Search .............. 73/290 V, 631, 900; 367/908, 163

[56] References Cited

U.S. PATENT DOCUMENTS

| | | | |
|---|---|---|---|
| 3,090,224 | 5/1963 | Rankin | 73/615 |
| 4,210,969 | 7/1980 | Massa | 73/290 V X |
| 4,221,004 | 9/1980 | Combs et al. | 367/908 X |
| 4,398,261 | 8/1963 | Saint-Oyant et al. | 73/900 |
| 4,470,299 | 4/1985 | Soltz | 367/908 X |

OTHER PUBLICATIONS

"Applications of the VCR", with AGC and Differential Amplifier Transfer Characteristics; Jacob Millman-Microelectronics Book, ©1979; pp. 404-406, 533-535.

Primary Examiner—Daniel M. Yasich
Attorney, Agent, or Firm—Michael Ebert

[57] ABSTRACT

An ultrasonic, echo-ranging instrument for measuring the level of liquid in an open channel or tank. The instrument includes a transducer disposed at a fixed position directly above the liquid surface, the nature of the gaseous environment therebetween determining the velocity of ultrasonic energy propagated therethrough. The transducer is excited to emit periodic pulses which are intercepted by the liquid surface and by a reference point a fixed distance from the transducer to produce both reference and liquid echo pulses that are returned to the transducer and detected thereby. The respective transit times of the reference echo and the liquid echo pulses are determined, and the ratio between these transit times is computed to provide an output representing the level of liquid independent of changes in the gaseous environment. To ensure accurate readings, the reference echo and liquid echo pulses from the transducer are fed to a single automatic gain control circuit whose operation is time shared. The circuit is enabled in a reference mode having a predetermined duration to effect gain control for the reference echo pulse and is thereafter enabled in a target mode having a predetermined duration to effect gain control for the liquid echo pulses.

4 Claims, 2 Drawing Figures

TIME-SHAPED AGC FOR ULTRASONIC LIQUID LEVEL METER OF THE ECHO-RANGING TYPE

Related Application

This application is a continuation-in-part of my copending application Ser. No. 337,082, filed Jan. 4, 1982, entitled "Ultrasonic Liquid Level Meter," (now U.S. Pat. No. 4,470,299) whose entire disclosure is incorporated herein by reference.

BACKGROUND OF INVENTION

1. Field of Invention

This invention relates generally to ultrasonic liquid level meters of the echo-ranging type that are compensated for environmental changes, and more particularly to a meter of this type which yields both reference and liquid level echo pulses and which includes a time-shared automatic gain control circuit to derive from these echo pulses, output pulses of constant amplitude to facilitate accurate measurement.

In an ultrasonic echo-ranging meter, pulses of ultrasonic energy transmitted from a transducer station placed above the surface of a liquid in a tank or open channel are reflected thereby to produce echo pulses which are received at the station. By determining the round trip transit time of the pulse energy in the gaseous medium above the liquid surface, which transit time depends on the distance between the station and the surface, one is able to provide a reading of liquid level.

The accuracy of an ultrasonic liquid level meter of the echo-ranging type is adversely affected by environmental changes; notably temperature, pressure and chemical composition. These factors alter the velocity of acoustic propagation. For example, the velocity sound in air at 0° C. is 1,087.42 fps, whereas in carbon dioxide it is 1,106 fps. When a meter is installed in an environment in which the chemical nature of the gaseous medium undergoes change, this factor will disturb the level reading unless means are provided to compensate or correct therefor. Similarly, changes in the temperature of the medium or in ambient pressure adversely affects the accuracy of the instrument.

In order to provide a reading in an echo-ranging liquid level meter, which is independent of changes in the propagation medium (air or other gas), Willis et al. U.S. Pat. No. 3,834,233, discloses a first transducer mounted on top of a tank to direct sound energy down into the tank and to detect an echo from the surface of the liquid therein.

To compensate for inaccuracies due to changes in the velocity of the sound, Willis et al. positions a second or reference transducer a fixed distance from the first to detect the transmitted wave. Detected signals derived from the two transducers are processed to cancel the effects of any variation in the velocity of sound due to environmental fluctuations.

In my copending patent application above-identified, compensation for environmental changes is effected by a reflector fixedly positioned to intercept and reflect energy from a side portion of the radiation field pattern of the transmitted beam to produce a reference echo signal which in no way interferes with the main liquid level echo signal derived from transmitted energy in a path normal to the surface of the liquid.

In the system disclosed in my copending application, the transducer is excited to emit periodic pulses which are directed along a center path toward the liquid surface and reflected to produce liquid echo pulses which return to the transducer and are detected thereby. The reference reflector which is placed at a predetermined position relative to the transducer intercepts energy from a side path in the radiation pattern of the transducer to return it to the transducer to produce reference echo pulses. Means are provided to determine the transit time along the center path and along the side path. The ratio of the reference side path and center path transit times is computed to provide an output representing the level of liquid independent of changes in the gaseous environment.

In prior art ultrasonic meters such as those disclosed in the Tankin U.S. Pat. No. 3,090,224, the Kritz U.S. Pat. No. 2,949,772, the Kohno U.S. Pat. No. 4,183,244 and the Asada U.S. Pat. No. 3,710,021, use is made of an automatic gain control circuit in conjunction with the received signals. Automatic gain is generally effected by a control circuit adapted to automatically modify the amplification gain of a receiver in a manner whereby the desired output signal remains at a constant amplitude despite variations in input signal strength.

In an ultrasonic echo-ranging liquid level meter, variations in the amplitude of the echo pulses received from the surface of the liquid are encountered by reason of changes in this surface as well as changes in distance due to liquid level changes. Thus an echo pulse which has a long distance to travel before reaching the transducer will be weaker than an echo pulse traveling a shorter distance.

But in the context of an echo-ranging system of the type disclosed in my copending application in which reference echo pulses as well as liquid level echo pulses are received, at first blush it would appear that no need exists for automatic gain control with respect to the reference echo pulses. Because these pulses are derived from a reflector having a smooth surface placed a fixed distance from the transducer, all reference echo pulses should have the same strength.

However, typical ultrasonic transducers of the same model, though seemingly alike, nevertheless differ somewhat in sensitivity and exhibit a wide spread in echo response. Thus when manufacturing an ultrasonic echo-ranging instrument, all of which incorporate the same model of transducer, it becomes necessary to make an individual gain setting to match a particular transducer to the instrument.

Thus in an environmentally-compensated ultrasonic instrument of the type disclosed in my copending application in which reference as well as liquid level echo pulses are received, actually two automatic gain control functions are needed: one for the reference echo pulses, and the other for the liquid level pulses.

SUMMARY OF INVENTION

In view of the foregoing, the main object of this invention is to provide an environmentally compensated ultrasonic instrument of the echo-ranging type for metering liquid level wherein reference echo pulses as well as the liquid level pulses are subjected to automatic gain control (AGC) to afford output pulses of constant amplitude to facilitate accurate measurement.

While the invention will be described in conjunction with an environmentally-compensated ultrasonic instrument which uses a side reflector to produce the reference echo pulses, it is to be understood that the invention is also useful with other forms of such instruments which produce reference echo pulses as well as liquid level echo pulses, such as those disclosed in the Massa U.S. Pat. No. 4,210,967; the Willis et al. U.S. Pat. No. 3,834,233; and the Adams et al. U.S. Pat. No. 4,130,018.

More particularly, an object of this invention is to provide an instrument of the above-type which makes use of a single automatic gain control circuit that is time shared to effect separate gain control for operation in the reference mode and in the liquid level or target mode.

A significant advantage of an AGC system in accordance with the invention is that it represents a more economical solution to the problem of gain control.

Briefly stated, these objects are attained in an ultrasonic, echo-ranging instrument for measuring the level of liquid in an open channel or tank. The instrument includes a transducer disposed at a fixed position directly above the liquid surface, the nature of the gaseous environment therebetween determining the velocity of ultrasonic energy propagated therethrough. The transducer is excited to emit periodic pulses which are intercepted by the liquid surface and by a reference point a fixed distance from the transducer to produce both reference and liquid echo pulses that are returned to the transducer and detected thereby. The respective transit times of the reference echo and the liquid echo pulses are determined, and the ratio between these transit times is computed to provide an output representing the level of liquid independent of changes in the gaseous environment. To ensure accurate readings, the reference echo and liquid echo pulses from the transducer are fed to a single automatic gain control circuit whose operation is time shared. The circuit is enabled in a reference mode having a predetermined duration to effect gain control for the reference echo pulse and is thereafter enabled in a target mode having a predetermined duration to effect gain control for the liquid echo pulses.

OUTLINE OF DRAWINGS

Figure 2:
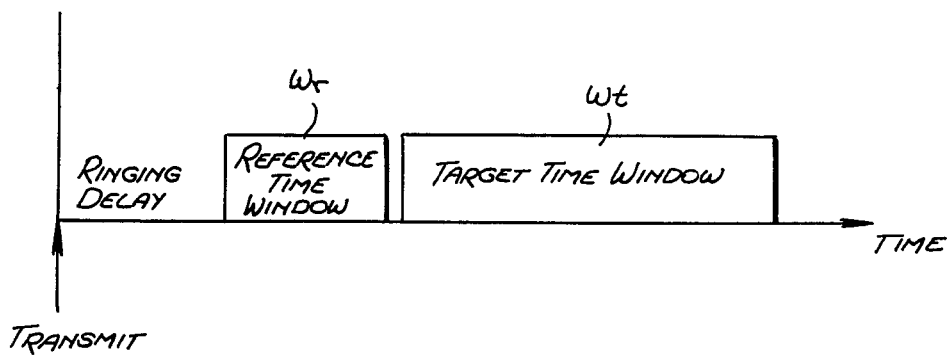

For a better understanding of the invention as well as other objects and further features thereof reference is made to the following detailed description to be read in conjunction with the accompanying drawings, wherein:

FIG. 1 is a block diagram of a time-shared AGC for an ultrasonic liquid level meter of the echo-ranging type in accordance with the invention; and FIG. 2 is a timing diagram of the system.

DESCRIPTION OF INVENTION

Referring now to FIG. 1, there is shown an open trough or channel 10 through which liquid 11 flows, the instrument in accordance with the invention serving to measure the level H of liquid in the channel. By placing a dam in the channel, the level of liquid attained downstream of the dam will depend on flow rate; hence by measuring this liquid level one can also determine the flow rate. In practice, instead of an open channel, the liquid whose level is to be measured may be that held in a process tank or other container. Consequently the atmosphere above the surface of the liquid is not necessarily pure air and may include ammonia, carbon dioxide and other gases.

Mounted above channel 10 at a station having a fixed distance Z from the bottom of the channel is an ultrasonic transducer 13. This may take the form of a piezoelectric transducer, a ceramic electrostatic unit or any other element capable of generating ultrasonic energy of adequate strength. The straight line distance B between the face of transducer 13 and the surface 12 of the liquid depends on the varying level H of the liquid. Thus the value of Z is constant, whereas the relative values of H and B vary but always add up to value Z.

The field radiation pattern produced by an ultrasonic transducer is related to the ratio of the transducer's ultrasonic wavelength to its diameter. Thus a large diameter-to-wavelength ratio produces a relatively narrow field pattern and a small ratio, a broad field pattern.

The field pattern produced by transducer 13 includes a center beam path which extends vertically from the transducer face to the surface of the liquid and is normal thereto. The center beam path represents the shortest distance between the transducer and the liquid surface, for all other paths in the radiation field pattern more or less diverge from normal and represent progressively longer distances.

Placed at a fixed distance from transducer 13 at a position to intercept a side path of energy in the radiation pattern is a reflector 14. The reflector produces an echo pulse that is returned to the transducer, its time of transit being a function of the distance of the reflector from the transducer and of the velocity of sound in the gaseous medium.

Transducer 13 is excited periodically by a transmitter 15, causing the transducer to emit periodic pulses of ultrasonic energy in the desired field pattern. The transmitted energy is propagated through the gaseous medium between the transducer and the liquid surface and it is directed toward the surface where it is reflected and returned to the transducer which now acts as a detector whose output is coupled to a receiver 16. In practice, a limiting diode is provided to protect receiver 16 from transducer 13 when it is being excited.

Each transmitted pulse is first followed in time by a reference echo pulse, for the reference distance from the transducer is shorter than the distance to the liquid surface. The reference echo pulse is follows by a liquid level pulse which is received over the center path, the shortest distance to the liquid surface. Actually, the instrument alternates between two modes; namely, reference and target. Each mode includes many, many consecutive transmit-receive cycles which are needed to establish an average value that corresponds to the particular mode.

The counter means by which one determines the transit time of ultrasonic pulse energy in its round trip from transducer 13 to the liquid surface target and the transit time in its round trip from the transducer to the reference point is set forth in detail in my copending application and will therefore not be repeated. The counts representing the liquid target transit time and the reference transit time are applied to a microcomputer 17 which determines the ratio of the reference and target transit times to yield an output count representing liquid level independent of the environmental changes.

In the arrangement shown in FIG. 1, an automatic gain control circuit 18 is interposed between transducer 13 and receiver 16, this circuit being enabled by microcomputer 17, which also controls the operation of transmitter 15. In the reference mode, the AGC is enabled only during time slot or windows corresponding to the reference mode during which a reference echo pulse is received. During target mode, the AGC is enabled during time windows corresponding to the target mode during which a liquid level echo pulse is received. The microcomputer is programmed to provide enabling signals to the AGC to establish these two time windows.

In operation, as shown in FIG. 2 by the timing diagram, the microcomputer begins an instrument cycle with a trigger actuating transmitter 15 to drive transducer 13, thereby producing an ultrasonic transmit pulse. After a brief ringing-decay-delay, the microcomputer enables AGC 18 during the time window $W_r$ for the reference mode. All echoes received during this time slot will affect the AGC gain level, which in turn conditions the proper echo pulse to be detected, to thereby establish a reference count. This transmit-receive cycle is repeated many times until the reference mode has been completed.

The target mode operation is carried out in a manner similar to the reference mode, except that in this case, the AGC is enabled during the liquid target mode window $W_t$.

Because the AGC requires updating each time a change in mode is effected, and this cannot be done instantaneously, it is necessary to disregard all echoes which are received while the AGC gain level is being updated. Thus, during the reference mode, the microcomputer is programmed to disregard the first several reference counts before computing an average reference value, and in the target mode the first several target counts are disregarded before computing an average target value. When valid reference and target data is available to provide the reference and target transit times, the ratio of these times is computed to provide accurate level or flow rate data.

While there has been shown and described a preferred embodiment of time-shared AGC for ultrasonic liquid level meter of the echo-ranging type in accordance with the invention, it will be appreciated that many changes and modifications may be made therein without, however, departing from the essential spirit thereof.

I claim:

1. An ultrasonic echo-ranging system to measure the level of a liquid in an open channel or other liquid container located in a gaseous environment subject to changes which affect the velocity of acoustic propagation; said sytem comprising:
   A. an ultrasonic transducer disposed at a fixed position directly above the liquid; the gaseous environment therebetween determining the velocity of ultrasonic energy propagated therethrough;
   B. means to excite the transducer to emit periodic pulses of ultrasonic energy which are directed toward the surface of the liquid and reflected from this target to produce liquid echo pulses which return to the transducer and are detected thereby;
   C. reference means at a fixed point relative to the transducer to intercept energy emitted from said transducer and return it to the transducer to produce reference echo pulses;
   D. receiver means coupled to the transducer to derive therefrom at different times said reference echo pulses and said liquid echo pulses, said receiver means including automatic gain control means responsive to said pulses to produce output pulses of constant amplitude representing the reference pulses and output pulses of constant amplitude representing the liquid pulses, said automatic gain control means being constituted by a single automatic gain control circuit which is enabled during a first time slot subsequent to the emission of a transducer pulse to operate on the received reference echo pulse and during a later second time slot to operate on the received liquid echo pulse whereby the operation of the circuit is time shared;
   E. measuring means responsive to said output pulses to measure the time elapsed between the emitted transducer pulse and a subsequent reference echo pulse to determine the reference transit time, and to measure the time elapsed between the emitted transducer pulse and a subsequent liquid echo pulse to determine the target transit time; and
   F. a computer coupled to the measuring means to calculate the ratio of the reference and target transit times and to yield an output representing the level of the liquid independent of change sin the gaseous environment.

2. A system as set forth in claim 1, wherein said time slots are created by said computer which so controls said automatic gain control circuit as to define a reference time window and a liquid target time window.

3. A system as set forth in claim 2, wherein said transducer has a diverging radiation field pattern, and said reference means is at a point intercepting energy from a side path in said pattern.

4. A system as set forth in claim 3, wherein said reference means is a reflector.

* * * * *